United States Patent [19]
Lezdey et al.

[11] Patent Number: 5,869,063
[45] Date of Patent: Feb. 9, 1999

[54] DERMATOLOGICAL AND COSMETIC COMPOSITIONS CONTAINING MARAMA BEAN EXTRACT

[75] Inventors: John Lezdey, Voorhees, N.J.; Allan Wachter, Tempe, Ariz.

[73] Assignee: Protease Sciences, Inc., Voorhees, N.J.

[21] Appl. No.: 107,565

[22] Filed: Jun. 29, 1998

[51] Int. Cl.$^6$ .............................. A61K 7/06; A61K 35/78
[52] U.S. Cl. ......................... 424/195.1; 424/74; 435/410
[58] Field of Search .................................. 424/195.1, 74; 435/410

[56] References Cited

U.S. PATENT DOCUMENTS 5,624,672 4/1997 Bathurst et al. ..................... 424/195.1
5,635,186 6/1997 Bathurst et al. ..................... 424/195.1

*Primary Examiner*—Herbert J. Lilling
*Assistant Examiner*—Deborah K. Ware
*Attorney, Agent, or Firm*—John Lezdey & Assoc.

[57] ABSTRACT

Compositions and methods are provided for treating the skin especially where it is placed in an environment which can cause injury or inflammation to the skin. The compositions contain an effective amount of the extract from marama beans.

10 Claims, No Drawings

1

DERMATOLOGICAL AND COSMETIC COMPOSITIONS CONTAINING MARAMA BEAN EXTRACT

FIELD OF THE INVENTION

The present invention relates to cosmetic and dermatological compositions containing marama bean extract. More particularly, there is provided cosmetic compositions which improve atmosphere damaged skin including chapped lips, wind burn, sun burn and wrinkles resulting therefrom.

BACKGROUND OF THE INVENTION

Marama beans, Tyosema esculentum, is classified in the Leguminosae family and the Caesalpinioideae sub-family. The marama plants grow in semi-desert climates in South Africa and Australia. Marama beans have a high level of trypsin inhibitors (239TUI/mg protein) which is about twice that reported for soybeans.

The antiprotease present in marama beans has recently been isolated and partially characterized. Beans were obtained from Southern Africa and were part of the same lot used in a nutritional study. The hard shells were cracked, the oily kernel removed and the inhibitor extracted essentially as described by Wagner and Rheim, 1967, using an ethanol wash and solubilization in dilute HCl. An ammonium sulfate cut was taken between 40 and 80 percent saturation, dialyzed and freeze dried. This fraction represented approximately 10% of the total protein in the bean. Analysis of this fraction on SDS acrylamide gels revealed a single but rather diffuse band with a molecular weight around 18,000.

The molecular weights of the proteinase inhibitors range between 20,000 to 27,000 at least five different trypsin inhibitors are present as well as two elastase inhibitors.

SUMMARY OF THE INVENTION

The present invention provides a dermatological and cosmetic composition for improving the texture of skin. The composition is especially useful for treating skin damaged by the atmosphere such as sun damaged or wrinkled skin, chapped lips or skin on face and hands, and for treatment after a chemical peel, for example with a hydroxy glycollic acid.

The compositions of the invention contain at least about one percent of the extract of marama beans. The amount of extract which can be used is about one percent by weight, preferably, about 1 to 10% by weight of composition.

The extract can be used in the form of a lotion, creme, gel or solution, depending on the use or treatment contemplated. The extract can be formulated into cosmetic compositions such as lipsticks, hand cremes, and the like.

The marama bean extract can be used alone or with other skin treatment compositions such as aloe vera.

It is a general object of the invention to provide a cosmetic and dermatological composition which contains an effective amount of the extract from marama beans.

It is another object to provide a cosmetic composition for treating sensitive skins.

It is yet another object to provide a topical composition which helps environmentally damaged skin.

It is a still further object of the invention to provide a method for improving environmentally damaged skin.

DESCRIPTION OF THE PREFERRED EMBODIMENTS

The present invention provides an improvement in cosmetic and dermatological compositions by providing a safe and natural tryptase and elastase inhibitor and which is derived from marama beans. The extract from the marama bean can be incorporated in most cosmetic compositions by conventional means. The extract is generally in the form of a liquid or a lyophilized powder and incorporated in an amount of at least one percent by weight of composition, preferably between about 1 to 10% by weight.

The favorable activity of the extract is believed to be the results of the tryptase and elastase inhibition present during inflammation. Also, the control of the elastase permits the laying down of new tissue without degradation resulting from the presence of elastase and Cathepsin G. After a chemical peel or removal of the upper dermal layer mechanically or naturally, the new tissue layer is more resilient and thereby reduces the wrinkles. In aging skin, the extract appears to moisturize as well as soften the existing skin. The compositions with the extract have a prophylactic effect and reduce the incidence of skin eruptions or inflammations as a result of the action against serine proteases.

The compositions according to the invention may be presented in all dosage forms normally used for topical application, in particular in the form of aqueous, aqueous-alcoholic or, oily solutions, of dispersions of the lotion or serum type, of anhydrous or lipophilic gels, of emulsions of liquid or semi-solid consistency of the milk type, obtained by dispersing a fatty phase in an aqueous phase (O/VV) or vice versa (VV/O), or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

They may also be used for the scalp in the form of aqueous, alcoholic or aqueous-alcoholic solutions, or in the form of creams, gels, emulsions or foams or alternatively in the form of aerosol compositions also containing a propellent agent under pressure.

The amounts of the different constituents of the compositions according to the invention are those traditionally used in the fields in question.

These compositions constitute, in particular, cleansing, protective, treatment or skin care creams for the face, hands, feet, major anatomical folds or the body (for example day creams, night creams, make-up removal creams, foundation creams, sun-protection creams), fluid foundations, make-up removal milks, protective or skin care body milks, after-sun milks, skin care lotions, gels or foams, such as cleansing or disinfecting lotions, bath compositions, deodorant compositions, aftershave gels or lotions, compositions or compositions for treating certain skin disorders such as those mentioned above.

The compositions according to the invention may also consist of solid preparations constituting cleansing bars or soaps.

The compositions may also be packaged in the form of an aerosol composition containing a propellent agent under pressure.

When the composition of the invention is an emulsion, the proportion of the fatty phase can range from 5% to 80% by weight, and preferably from 5% to 50% by weight, relative to the total weight of the composition. The oils, emulsifiers and coemulisifiers used in the composition in emulsion form are chosen from those traditionally used in the cosmetics. The emulsifier and the coemulsifier are present in the composition in a proportion ranging from 3% to 30% by weight, and preferably 5% to 30% or, better still, from 0.5% to 20%, by weight relative to the total weight of the composition. The emulsion can, in addition, contain lipid vesicles.

When the compositions of the invention is an oily gel or solution, the fatty phase can represent more than 90% of the total weight of the composition.

In a known manner, the composition of the invention may also contain adjuvants which are customary in the cosmetics, such as hydrophilic or lipophilic gelling agents, hydrophilic or lipophilic active agents, preservatives, antioxidants, solvents, perfumes, fillers, screening agents, bactericides, odor absorbers and coloring matter. The amounts of these different adjuvants are those traditionally used in the cosmetic, or dermatological field, and are, for example, from 0.01% to 10% of the total weight of the composition. Those adjuvants, depending on their nature, may be introduced into the fatty phase, into the aqueous phase and/or into lipid spherules.

As oils which can be used in the invention, mineral oils (liquid paraffin), vegetable oils (liquid fraction of shea butter, sunflower oil), animal oils (perhydrosquatene), synthetic oils (Purcellin oil), silicone oils (cyclomethicone) and fluorinated oils (perfluoro polyethers) may be mentioned.

Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture sold under the name Tefose® 63 by the company Gattefosse may be mentioned as examples.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allanloin, sugars and sugar derivatives, water-soluble vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used.

The compositions of the invention may include other plant or herbal extracts. For example, there may be utilized extracts of Paraguay tea, Kola and Guarana which provide a source of methylxanthines, saponius, tannins and glycosides which have been shown to reduce swelling and redness. The extract of Paraguay tea is known as "Mate extract" and is described in the "International Cosmetic Ingredient Dictionary", 5th Edition. Mate extract is commercially available in combination with extracts of Kola and Guarana which is sold by Cosmetic Ingredient Resources of Stamford, Conn. under the trademark "QUENCHT".

Each of mate extract, marama bean extract and aloe vera extract are known to provide anti-infalmmatory activity. The anti-elastase and anti-tryptase activity of marama bean extract provides a synergistic effect in treating skin inflammations.

A surfactant can be included in the composition so as to provide deeper penetration of the ingredients. Although natural surfactants are preferred, others such as isopropyl myristate can be used.

Other plant ingredients may be used, preferably, in amounts from about 0.5 to 2% by weight.

The following examples illustrating the compositions of the invention are not intended to limit the scope of the invention. The amounts indicated are by weight percent unless otherwise noted.

Example 1

EXAMPLE 1

A gel is prepared by admixing the following ingredients.

| Ingredient | Wt % |
|---|---|
| Carbomer 940 | 2.10 |
| Xantham gum | 0.15 |
| Propylene glycol | 51.94 |
| Dipropylene glycol | 10.00 |
| Ethoxydiglycol | 15.00 |
| Dimethylisosorbide | 10.00 |
| Aloe Vera gel | 2.00 |
| Surfactant | 0.05 |
| Marama bean extract | 9.76 |
| | 100% |

This composition is useful to reduce wrinkles or after a chemical skin peel.

EXAMPLE 2

A gel is prepared by admixing the following ingredients:

| | Ingredient | Wt % |
|---|---|---|
| 1. | Propylene Glycol | 51.94 |
| 2. | Carbomer 940 | 2.10 |
| 3. | Dipropylene glycol | 10.00 |
| 4. | Xanthan gum | 0.15 |
| 5. | Ethoxydiglycol | 15.00 |
| 6. | Dimethylisosorbide | 10.00 |
| 7. | Ascorbic Acid | 2.00 |
| 8. | Chloroxylenol | 0.20 |
| 9. | Linoleamidopropyl PG-diammonium chloride phosphate | 1.50 |
| 10. | Glycereth 4.5 Lactate | 2.00 |
| 11. | Aloe Vera Gel | 2.00 |
| 12. | Marama bean extract (lyophilized) | 2.00 |
| 13. | Tetrasodium EDTA | 0.10 |
| 14. | Citric Acid | 0.010 |
| 15. | Cocamidopropyl PG-dimonium chloride phosphate | 1.00 |

Ingredients 1 and 2 are mixed to disperse and form a gel. About 80% of ingredient 3 is mixed with ingredient 4, added to the gel and heated with mixture to 47 degrees C. The balance of 3 is mixed with ingredients 5–10 and added to the gel. Ingredients 11–15 are then admixed and added to the gel at 38 degrees C. After mixing, the gel is brought to room temperature.

This gel composition can be used as an after-sun treatment.

EXAMPLE 3

A lotion is prepared by admixing the following ingredients:

| Ingredient | Wt % |
|---|---|
| Propylene Glycol Stearate | 9.50 |
| Isocetyl alcohol | 5.00 |
| PEG-100 Stearate | 1.20 |
| Water | 69.90 |

-continued

| Ingredient | Wt % |
| --- | --- |
| Methyl paraben | 0.20 |
| Propylene glycol | 13.10 |
| Sorbitan palmitate | 0.60 |
| Marama bean extract | 6.00 |
| Mate extract | 0.50 |
| | 100% |

The lotion can be used to treat chapped hands and to soften psoriatic sores.

EXAMPLE 4

An anti-wrinkle cream is prepared by mixing the following ingredients:

| Ingredient | Wt % |
| --- | --- |
| Glycerol stearate | 11.0 |
| PEG-100 stearate | 2.0 |
| Cetostearyl alcohol | 2.5 |
| Disodium EDTA | 0.1 |
| Methyl Paraben | 0.1 |
| Propylene glycol | 11.0 |
| Sorbitan stearate | 0.7 |
| Marama bean extract (lyophilized) | 2.5 |
| Aloe vera gel | 2.0 |
| Water | 8.5 |
| | 100% |

EXAMPLE 5

An after-sun is prepared by admixing the following ingredients:

| Ingredient | Wt % |
| --- | --- |
| Carbomer | 2.80 |
| Propylene Glycol | 92.05 |
| Disodium EDTA | 1.10 |
| Methyl Paraben | 0.20 |
| Marama bean extract (lyophilized) | 2.00 |
| Mate extract | 0.35 |
| Aloe Vera Gel | 2.50 |
| | 100% |

EXAMPLE 6

A solution according to the invention is prepared by admixing the following ingredients:

| Ingredient | Wt % |
| --- | --- |
| Ethoxyglycol | 15.00 |
| Propylene Glycol | 35.00 |
| Ethanol | 25.00 |

-continued

| Ingredient | Wt % |
| --- | --- |
| Water | q.s. |
| Disodium EDTA | 0.10 |
| Marama bean extract (lyophilized) | 4.50 |
| Aloe Vera Gel | 1.75 |
| | 100% |

EXAMPLE 7

A shampoo is prepared by admixing the following ingredients:

| Ingredient | Wt % |
| --- | --- |
| C12-15 Pareth-7 Carboxylic Acid | 10.0 |
| Isosteareth -6 carboxylic Acid | 5.0 |
| Hexylene Glycol | 8.0 |
| Chloroxylenol | 0.5 |
| Marama bean extract (lyophilized) | 2.0 |
| Mate Extract | 0.5 |
| Aloe Vera Gel | 2.0 |
| Na2 EDTA | 0.1 |
| Water | 71.9 |
| | 100% |

The shampoo is useful in the treatment of scalp inflammation or itch.

The shampoo can be used for sensitive scalps which have sensations of purities, that is to say by itching or prickling to different factors such as inflammation triggered by local factors such as soaps, surfactants, erythema, and the like.

What is claimed is:

1. A cosmetic and dermatological composition which comprises an effective amount of an extract of marama beans to provide an anti-elastase or anti-tryptase treatment to skin.

2. The composition of claim 1 comprising at least one percent by weight of said extract.

3. The composition of claim 2 comprising about 1 to 10% by weight of said extract.

4. The composition of claim 1 in the form of a lotion, creme or gel.

5. The composition of claim 1 including aloe vera.

6. The composition of claim 1 which is a shampoo.

7. A method of treating sensitive skin which comprises topically applying a composition containing the extract of marama beans according to claim 1.

8. The method of claim 7 wherein said composition is applied after a chemical peel.

9. A method of claim 7 wherein said sensitive skin comprises chapped skin.

10. A method for reducing wrinkles in the skin which comprises topically applying to the site of the wrinkles an effective amount of the composition of claim 1.

* * * * *